United States Patent
Leung (10) Patent No.: US 11,391,743 B2
(45) Date of Patent: Jul. 19, 2022

(54) PERSONALIZED HEALTHCARE P4 CARDIAC HEALTH AND WELLNESS MONITORING SYSTEM AND METHOD UTILIZING TMAO AND TROPONIN

(71) Applicant: eNano Health Limited, Hong Kong (HK)

(72) Inventor: Patrick Shau-park Leung, Arcadia, CA (US)

(*) Notice: Subject to any disclaimer, the term of this patent is extended or adjusted under 35 U.S.C. 154(b) by 0 days.

(21) Appl. No.: 16/374,828

(22) Filed: Apr. 4, 2019

(65) Prior Publication Data

US 2019/0219595 A1 Jul. 18, 2019

Related U.S. Application Data

(63) Continuation-in-part of application No. 15/469,138, filed on Mar. 24, 2017, now Pat. No. 10,513,725, and
(Continued)

(51) Int. Cl.
| | |
|---|---|
| *G01N 33/68* | (2006.01) |
| *G01N 21/80* | (2006.01) |
| *G16H 50/30* | (2018.01) |
| *G01N 33/92* | (2006.01) |
| *G01N 33/94* | (2006.01) |

(Continued)

(52) U.S. Cl.
CPC ......... *G01N 33/6887* (2013.01); *G01N 21/80* (2013.01); *G16H 50/30* (2018.01);
(Continued)

(58) Field of Classification Search
CPC ............... G01N 33/6887; G01N 21/80; G01N 33/6848; G01N 2333/4712; G01N 33/94;
(Continued)

(56) References Cited

U.S. PATENT DOCUMENTS

| 8,748,104 B1 * | 6/2014 | Leung | C12Q 1/6883 435/198 |
|---|---|---|---|
| 2008/0032411 A1 * | 2/2008 | Lawrence | G01N 33/521 436/111 |

(Continued)

OTHER PUBLICATIONS

"A DIY medical diagnosis app" Mar. 23, 2014, weblink: https://www.kurzweilai.net/a-diy-medical-diagnosis-app accessed on Dec. 19, 2019 (Year: 2014).*
(Continued)

*Primary Examiner* — Dennis White
(74) *Attorney, Agent, or Firm* — Bioinnovation Legal PLLC; James C. Schroeder (57) ABSTRACT

The claimed invention provides real-time and subsequent analysis personalized user based caradiac health and wellness detection information utilizing novel cardiac health markers including Troponin as well as TMAO. Non-invasive techniques utilize saliva for body levels of cardiac wellness indicators as well as pharmaceutical ingestion which are coordinated over time. Saliva captured on sample strips are real-time indicator reviewed and subsequently analyzed using traditional analytical chemistry techniques including liquid chromatography/mass spectrometry (LC/MS) and coordinated with time of administration with optional genetic sequence analysis to confirm related cardiac disease conditions. By using P4 (Participatory, Personalized, Predictive, and Preventive) health management techniques the patient determines if the pharmaceutical is having the correct and desired effect for maximum therapeutic benefit. While illustrative embodiments detecting TMAO and Troponin are provided the system has broad cardiac wellness monitoring applicability.

1 Claim, 10 Drawing Sheets

Specification includes a Sequence Listing.

An illustrated diagram of KT3 & P4 combo test

Related U.S. Application Data a continuation-in-part of application No. 15/056,163, filed on Feb. 29, 2016, now Pat. No. 10,506,954.

(60) Provisional application No. 62/653,547, filed on Apr. 5, 2018.

(51) Int. Cl.
   *C12Q 1/54* (2006.01)
   *C12N 15/115* (2010.01)

(52) U.S. Cl.
   CPC .............. *C12N 15/115* (2013.01); *C12Q 1/54* (2013.01); *G01N 33/6848* (2013.01); *G01N 33/92* (2013.01); *G01N 33/94* (2013.01); *G01N 2333/4712* (2013.01)

(58) Field of Classification Search
   CPC ........ G01N 33/92; G16H 50/30; G16H 20/10; G16H 50/20; C12N 15/115; C12Q 1/54
   See application file for complete search history.

(56) References Cited

U.S. PATENT DOCUMENTS

| | | | | |
|---|---|---|---|---|
| 2013/0236978 | A1* | 9/2013 | Kalns | C07K 7/06 436/86 |
| 2014/0235963 | A1* | 8/2014 | Edwards | A61B 5/0022 600/301 |
| 2014/0296089 | A1* | 10/2014 | Holmes | G01N 35/026 506/9 |

OTHER PUBLICATIONS

Suzuki et al,"Trimethylamine N-oxide and prognosis in acute heart failure" Heart 2016;102:841-848 (Year: 2016).*

Yetisen et al,"A smartphone algorithm with inter-phone repeatability for the analysis of colorimetric tests" Sensors and Actuators B 196 (2014) 156-160 (Year: 2014).*

* cited by examiner

An illustrated diagram of KT3 & P4 combo test

PERSONALIZED HEALTHCARE P4 CARDIAC HEALTH AND WELLNESS MONITORING SYSTEM AND METHOD UTILIZING TMAO AND TROPONIN

CITATION LIST

Patent Literature

This patent application claims priority to provisional patent application 62/653,547 filed Apr. 5, 2018. Furthermore this patent application is a continuation-in-part and claims priority to U.S. patent application Ser. No. 15/666,699 filed Aug. 2, 2017 to Patrick Shau-park Leung entitled "Personalized Glucose and Insulin Monitoring System." In addition, this patent application is a continuation-in-part and claims priority to U.S. patent application Ser. No. 15/469,138 filed Mar. 24, 2017 to Patrick Shau-park Leung entitled "Public personalized mobile health sensing system, method and device" which is a continuation of U.S. patent application Ser. No. 15/056,163 filed Feb. 29, 2016 to Patrick Shau-park Leung entitled "Mobile automated health sensing system, method and device".

TECHNICAL FIELD

The claimed invention relates to biomedical healthcare patient monitoring based upon the P4 (Participatory, Personalized, Predictive, and Preventive) health management method. With greater particularity, the claimed invention addresses personalized healthcare monitoring of cardiac wellness indicators including TMAO and Troponin as well as optional prescription pharmaceuticals as well as illicit drug monitoring with patient alerting and artificial intelligence data interpretation.

BACKGROUND ART

Traditional biomedical monitoring of cardiac wellness indicators is often clinical in nature with results ordered by a doctor in a hospital or medical office setting and performed in a centralized laboratory setting. Even when patients are informed as to the blood levels of their cardiac indicator body chemistry it is often through the lens of the primary medical provider.

Using traditional methods, if a patient wishes to know detailed information about personal cardiac wellness levels in the body they must first schedule an office visit. Absent an emergency, such visits usually take place weeks to months after the request is made. To determine body levels of wellness indicators, blood is drawn and sent to an outside laboratory. Several days later the results are reported back to the primary healthcare physician who interprets the laboratory results and provides a high level summary to the patient.

Despite the rapid expansion of 'big data' healthcare information, patients are rarely the owners or curators of their own healthcare information leading to reduced choices and far fewer options in healthcare data portability when seeking out alternate providers.

SUMMARY OF INVENTION

Technical Problem

Current systems for monitoring of cardiac wellness indicator levels in the human body are centralized and exclusionary. They are not participatory apart from the blood sample that the patient provides for testing. Reporting of cardiac wellness indicator levels are not personalized in that apart from the unique data itself released by a medical healthcare provider, the medical service provider controls the manner, method and timing of information content release. The technical problems of cardiac wellness indicator level monitoring are primarily systematic in nature due to legal and healthcare provider process constraints around the information itself.

Apart from information distribution restrictions, drawing of patient blood in a clinical setting creates a number of challenges including sample perishability, hazardous waste disposal and personal bias against invasive procedures. Traditional laboratory nitrocellulose paper is often unsuitable for sample collection conjugated with analytical reporting chemicals.

Solution to Problem

By embracing the P4 (Participatory, Personalized, Predictive, and Preventive) health management method, the claimed invention provides patient engaging cardiac wellness indicator information by leveraging real-time and subsequent analytical measurements of TMAO and Troponin indicators. By utilizing patient saliva samples which are locally analyzed then transported to a centralized analysis facility, TMAO, Troponin and optional pharmaceutical and pharmaceutical carrier information is accurately captured and rapidly delivered to the patient using a smartphone or personal computing device.

Patient cardiac wellness level information is non-invasively obtained by saliva samples collected on disposable sample means including lateral flow strips. Local analysis is complemented by using traditional laboratory equipment including Liquid Chromatography/Mass Spectrometry (LC/MS), TMAO and Troponin as well as optional pharmaceutical and carrier levels are obtained and reported back to the patient directly using secure internet data transmission techniques. Enhancements to salivary sample capture in combination with analytical reporting chemicals include optimized lateral flow strip material.

Advantageous Effects of Invention

By empowering the patient to cultivate their own cardiac wellness body level information, predictive and preventative wellness is enabled. The claimed invention is distinguishable from using traditional blood level monitoring due to the powerful wellness knowledge enabled by calculating Troponin levels in real time obtained by the saliva/lateral flow sample conjugate with TMAO and additional results subsequently analyzed by LC/MS and ELIZA. Unlike traditional diagnostic kits, the claimed Troponin cardiac marker is novel and measured by aptamer in real-time enabling rapid and immediate cardiac wellness information to a patient in need thereof.

Moreover, in a doctor's office the drawn blood sample reflects a single point of time measured infrequently separated by months or years. In the claimed invention, the time of sample collection is known. With regular patient monitoring it is an expected and intended consequence that over-administration of pharmaceutical products (by patients forgetting if they had taken their medication and inadvertently re-administering it) as well as omitting pharmaceutical administration will be detectable and reportable to the patient and relevant family members and health care providers. In addition, patient privacy is maintained as no patient identifiable information needs to be included in the collection device when it is independently analyzed.

By combining the novel Troponin aptamer marker indicative of cardiac distress with subsequent analytical chemical characterization of TMAO via LC/MS and/or genetic sequencing, a novel, broad and robust cardiac health and wellness system is placed in the hands of the end consumer rather than viewed through the infrequent and often fragmentary lens of the medical provider.

BRIEF DESCRIPTION OF DRAWINGS

The accompanying drawings are included to better illustrate exemplary embodiments of the claimed invention.

DESCRIPTION OF EMBODIMENTS

P4 Medicine is Predictive, Preventive, Personalized and Participatory. Its two major objectives are to quantify wellness and demystify disease. In the illustrative examples contained herein, the aims of P4 Medicine are achieved by combining end-user analysis of current cardiac health metrics indicated by Troponin aptamer together with follow-on lab analytics of the same saliva sample to determine body levels of TMAO and administered pharmaceuticals. In a first illustrative example, user health data is gathered by smartphone to capture pharmaceutical administration and related health details such as time food intake.

Optionally, the system may be combined with glucose measuring within the same lateral flow test strips to report glucose levels to the end-user for personalized and participatory cardiac wellness monitoring. The same test strip subsequently analyzed using standard analytical equipment, however, provides the opportunity for predictive and preventative health screening based upon detection of TMAO and pharmaceuticals and their carriers as well as DNA, RNA and protein indicators of body health as well as the presence or absence of harmful bacteria, viruses and other disease carriers.

EXAMPLES

In addition to real-time cardiac health Troponin monitoring combined with analytical laboratory provided TMAO levels, the optimal management of health using correct pharmaceutical dosing and timing of administration is best managed by the patient. Unfortunately, patients rarely have access to the clinical tools needed for optimal pharmaceutical administration. The first illustrative example depicts the administration of the drug metformin so that using the claimed invention the patient can match drug dosing so that it is optimal for food intake. While metformin is utilized as an illustrative example the claimed invention is not intended to be limited to a particular pharmaceutical but instead intended for broad cardiac health management opportunities.

EXAMPLES

Example 1

Figure 1:
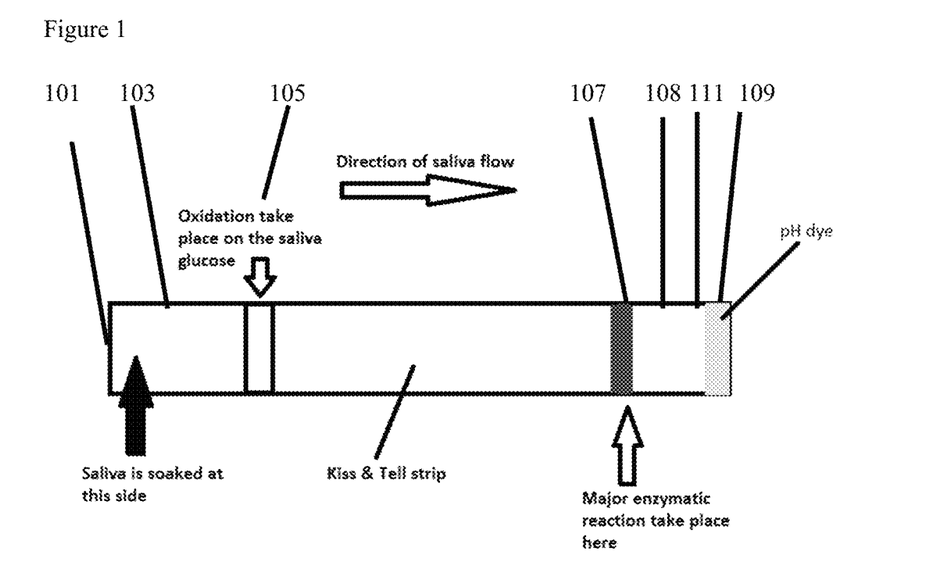
FIG. 1 is a top level schematic illustration of saliva capture lateral flow test strip with enhanced functionality.

The claimed P4 cardiac health and wellness platform is based upon salivary capture and analysis using one or more disposable lateral flow test strips. FIG. 1 depicts salivary test strip (101) which captures saliva (not shown) at salivary capture area (103) which is distributed by lateral flow into oxidation region (105) and onto enzymatic region (107) concluding with optional pH region (109). In the first illustrative embodiment the local enzymatic analysis provides locally measurable salivary indicator levels and incorporates optional antibody indicator region (108) as well as Troponin aptamer indicator region (111).

In the first illustrative example, cardiac health indicator levels of Troponin are captured by placing test strip (101) in a user's mouth (not shown) for two minutes to distribute saliva (not shown) to test strip (101). Adequate saliva capture is confirmed by illumination of pH region (109). In the first illustrative example, the user waits an additional three minutes upon which a measurable color change takes place at enzymatic region (107). Salivary indicator levels may be estimated by user color comparison visually or by computer analysis by a smartphone type device (not shown). Troponin aptamer indicator region (111) provides aptamers capable of binding to the skeletal Troponin I protein which is useful for diagnostics of skeletal muscle damage indicated by the skeletal Troponin I protein.

Figure 2:
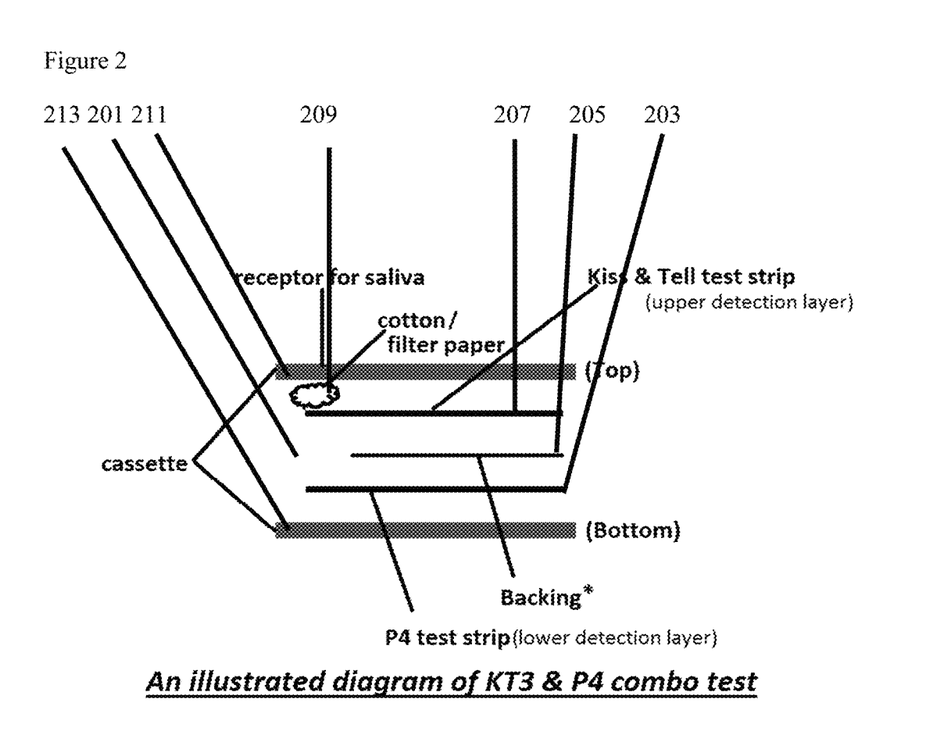
FIG. 2 is a side view schematic illustration of saliva capture lateral flow test strip with additional functionality.

The detection of salivary glucose is based on a coupling reaction between glucose oxidase and peroxidase. Glucose oxidase oxidizes the salivary glucose into gluconolactone and hydrogen peroxide (H2O2). In the presence of peroxidase, 10-acetyl-3,7-dihydroxyphenoxazine reacts with H2O2 in a 1:1 stoichiometry in order to produce a white to pink color. In a preferred embodiment, the chemical sensor at enzymatic region (107) is a compound having the following structural formula:

In the first illustrative embodiment, the salivary test strip may be single purpose as illustrated by salivary test strip (101) depicted by FIG. 1 or multi-purpose as illustrated by multi-function salivary test strip (201) depicted in FIG. 2. FIG. 2 multi-function salivary test strip (201) is multi-layer with top analytical layer (207), layer divider (205) backing and lower analytical layer (203). Saliva access is provided through optional cassette housing (213) with salivary receptacle (211) which distributes saliva (not shown) through optional saliva wicking material (209) which can be cotton, filter paper or other material suitable for distribution of saliva. In a preferred embodiment, optimized analytical lateral flow material is utilized for top analytical layer (207)

for real time enzymatic and aptamer detection and lower analytical layer (203) for subsequent off-line lab based enzymatic, LC/MS, antibody or genetic sequencing. The lateral flow analytical strip is distinguishable from traditional nitrocellulose filter paper by absorbency rate and internal composition. Distinguishable characteristics from traditional nitrocellulose paper include high hydrophilic behavior wicking 4 cm in under 50 seconds. Optimal analytical flow material characteristics include highly efficient body fluid separation with no analyte interference, excellent release with both latex and gold conjugates, reaction membrane to capture reagents bound to the immobilized latex beads combined with conjugate and analyte to give intense capture lines and superior sample wicking with no loss of assay sensitivity when compared to other materials and acting as an absorbent to liquids. Saliva is unlike blood in that it is stable at room temperature for long periods of time, safe to collect and transport and not considered medical waste.

In the present embodiment, as the aptamers and the skeletal Troponin I protein have high affinity (which is in the nanomolar range) and high specificity, the aptamers are capable of recognizing the skeletal Troponin I protein in the sample. In addition, being DNA fragments, the aptamers are not easily influenced by environmental factors such as external temperature, humidity, and the like. That is, the embodiments herein are more stable to extreme conditions (e.g., temperature, humidity) which make them more suitable to use in extreme environments, more stable for longer periods of transport and storage, and thus provide more consistent use and performance than existing methods. In addition, the stability of aptamer is greater than that of antibody, due to the nature of DNA oligo. The great stability of aptamer ensures the simple handling, and high quality of the detections. The detection method for the skeletal Troponin I protein in the present embodiment therefore has high sensitivity, high stability, and high accuracy compared to existing methods known in the art.

Figure 3:
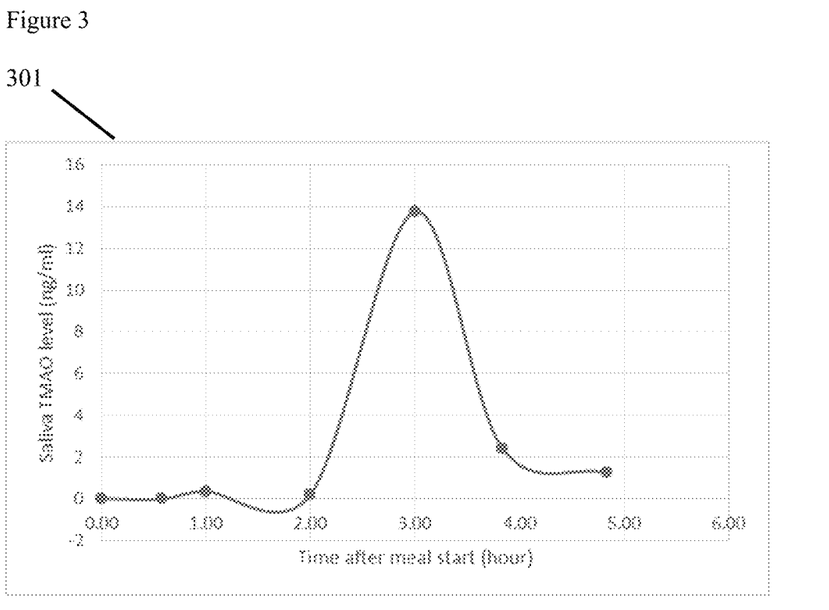
FIG. 3 is a graphical chart illustration of patient TMAO levels over time.

FIG. 3 reflects TMAO results in a Diabetic Patient after meal according to the claimed invention. TMAO results (301) indicate the substantial and health relevant rise in TMAO levels subsequent to eating food groups high in TMAO activity s reflected in Table 1.

TABLE 1

| QRcode | Time | TMAO1 | TMAO2 | TMAO3 | TMAO4 |
|---|---|---|---|---|---|
| 100002486 | 0910 | 0 | 0.0146 | 0 | 0 |
| 100002487 | 0945 | 0 | 0.0556 | 0 | 0 |
| 100002488 | 1010 | 0.292 | 0.406 | 0.34 | 0.385 |
| 100002489 | 1110 | 0.289 | 0.467 | 0 | 0.119 |
| 100002490 | 1210 | 14.9 | 17.1 | 12.6 | 12.3 |
| 100002491 | 1300 | 2.38 | 2.48 | 2.33 | 2.52 |
| 100002492 | 1400 | 1.27 | 1.3 | 1.03 | 1.24 |

Salivary levels of TMAO (trimethylamine-N-oxide), a metabolite derived from gut bacteria, provide predictive risk assessment indicators for cardiac health in patients who appear otherwise healthy. In the illustrative example, TMAO levels are demonstrated based upon ingestion of seafood present in traditional Chinese food. In the illustrative embodiment, TMAO levels are determined by subsequent LC/MS analysis. TMAO is a compound produced by the liver after intestinal bacteria digest certain nutrients: L-carnitine (found in red meat) and lecithin (found in egg yolks, meats and full-fat dairy products). Lecithin is also found in the intestines as a component of bile. The higher a patient's level of TMAO is, the more susceptible the individual is to accumulation of cholesterol in the artery wall which consequently increases risk factors for a cardiac event.

Example 2

Figure 4:
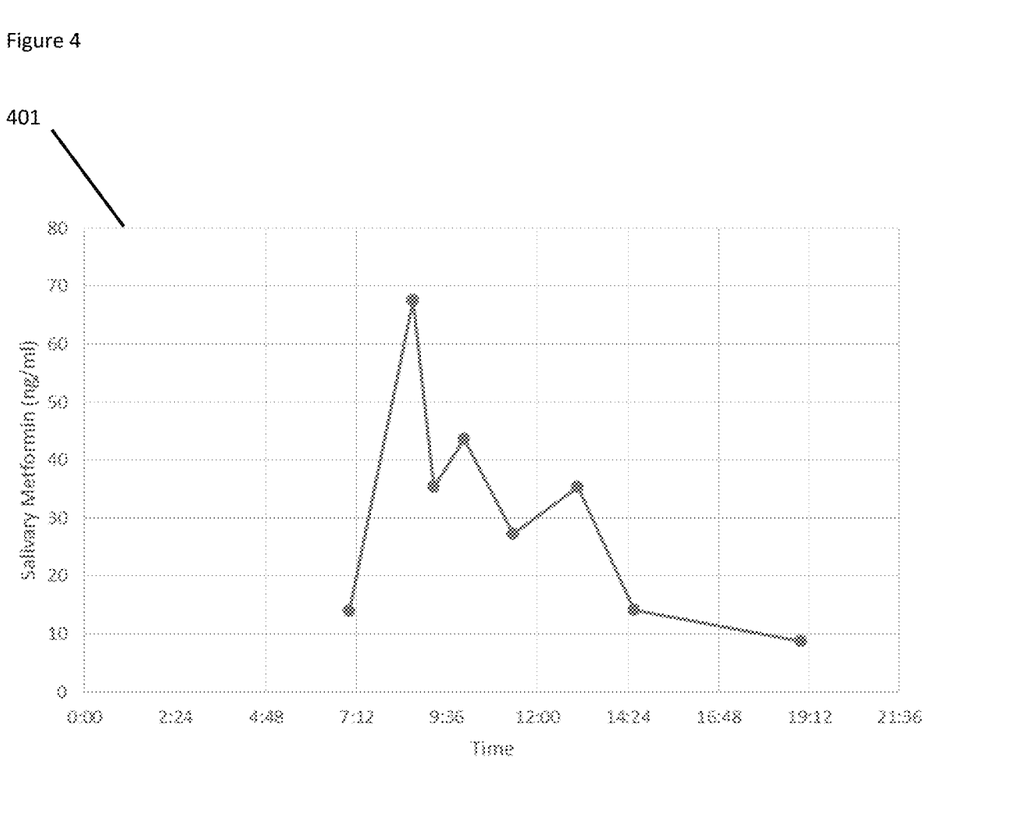
FIG. 4 is a graphical chart illustration of saliva derived pharmaceutical metformin levels over time.
Figure 5:
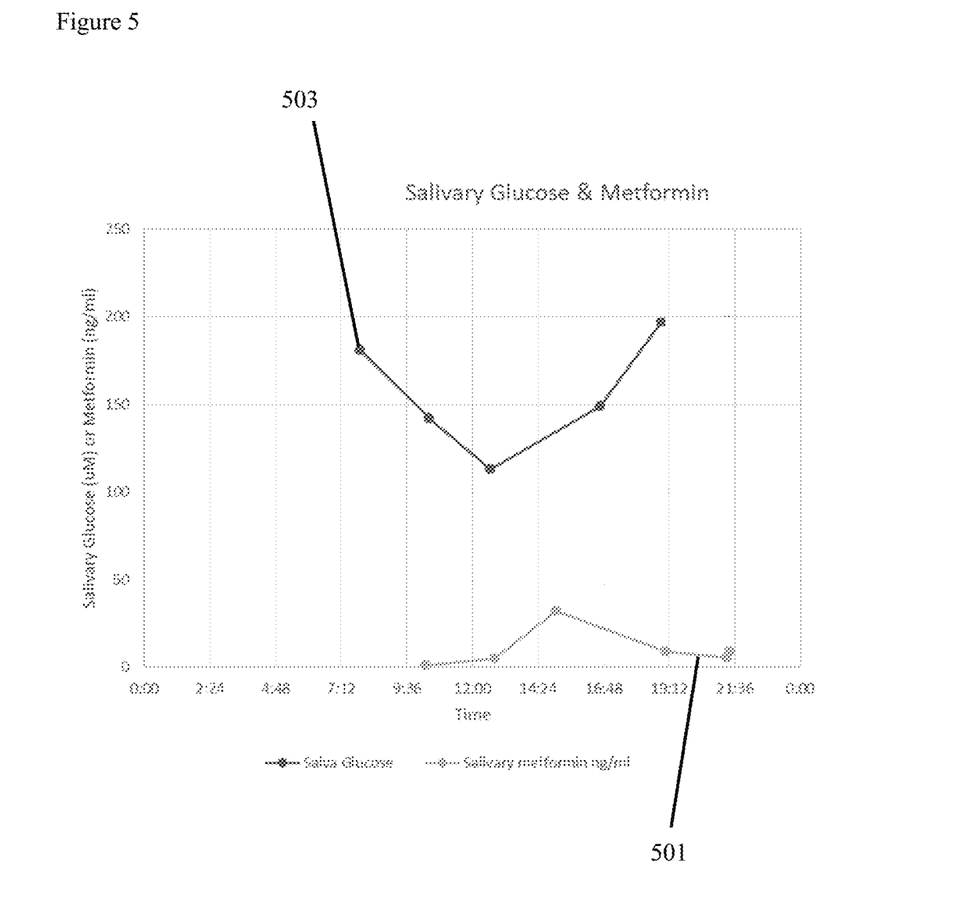
FIG. 5 is a graphical chart illustration of patient pharmaceutical and glucose levels over time.

Metformin (Metformin hydrochloride) is a type of medicine known as a biguanide. The drug works to lower the amount of sugar in the blood of people with diabetes. It does this by lowering the amount of sugar produced in the liver, and also increasing the sensitivity of muscle cells to insulin. FIG. 4 illustrates (401) traditional metformin administration which results in imprecise and inefficient pharmaceutical administration owing to the absence of guidance from the claimed invention. FIG. 5 illustrates metformin levels (501) in the body depicted as a function of time and plotted against corresponding glucose levels (503). Administration of metformin traditionally utilizes a 'best guess' of when the drug will be at optimum therapeutic levels. In the illustrative example representative FIG. 5 the pharmaceutical level to body condition graphical peaks are not aligned.

In preferred embodiment Example 2 detailed below a user captures glucose data in near real time utilizing a plurality of multi-function salivary test strips which are subsequently remotely analyzed for metformin. It is a direct and intended consequence of the claimed invention that measuring pharmaceutical levels and glucose from saliva provides more immediate and relevant composite wellness picture owing to the delay between meal ingestion and corresponding blood levels. In the second illustrative example the user is able to locally capture glucose information shortly after sample exposure.

To obtain pharmaceutical levels of metformin in the second illustrative example sample test strip (201) is mailed to a remote location for further analysis using traditional laboratory equipment such as LC/MS. Local analysis of glucose is by illustration only and not by limitation as any target capable of local enzymatic, aptamer and/or antibody analysis may be captured. By using a smartphone to input time of saliva sample data capture as well as most recent mealtime, glucose results are immediately captured and metformin results are subsequently returned to generate results allowing the user to determine general wellness indicators including ideal time for metformin pharmaceutical administration. One goal of this embodiment of the claimed invention is to allow the patient to best align the maximum therapeutic effect of metformin for processing of blood glucose after a meal is eaten by the patient. An additional primary objective is the capture of and reporting cardiac risk factors as indicated by Troponin and TMAO.

Figure 6:
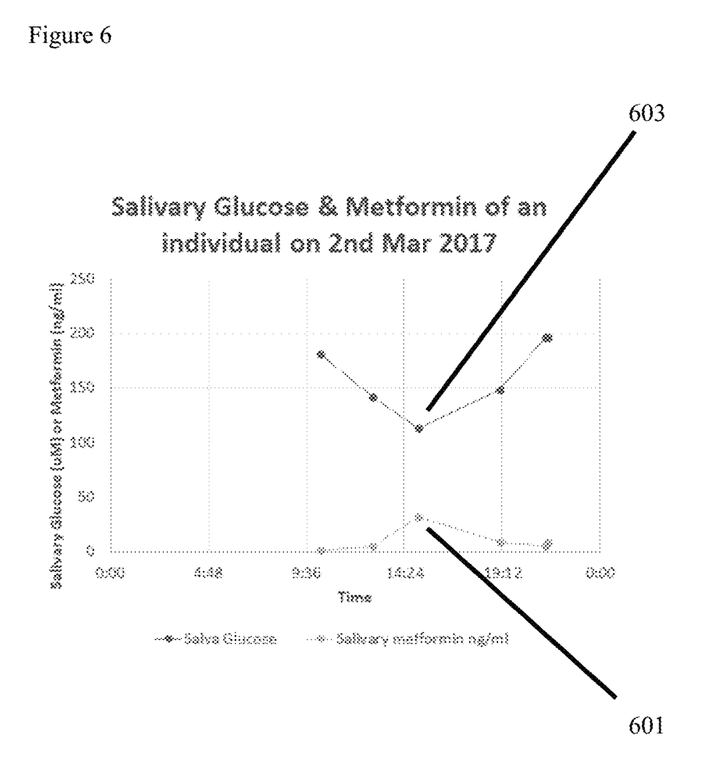
FIG. 6 is a graphical chart illustration of saliva derived body pharmaceutical content plotted by time.

In FIG. 6 the drug level to body condition graphical peaks are enabled and optimized due to feedback from the claimed invention. Through active body salivary chemistry analysis and pharmaceutical administration tracking achieved through use of the claimed invention, the optimal dosing is achieved by aligning the peak pharmaceutical level (601) with lowest amount of salivary glucose (603).

Figure 7:
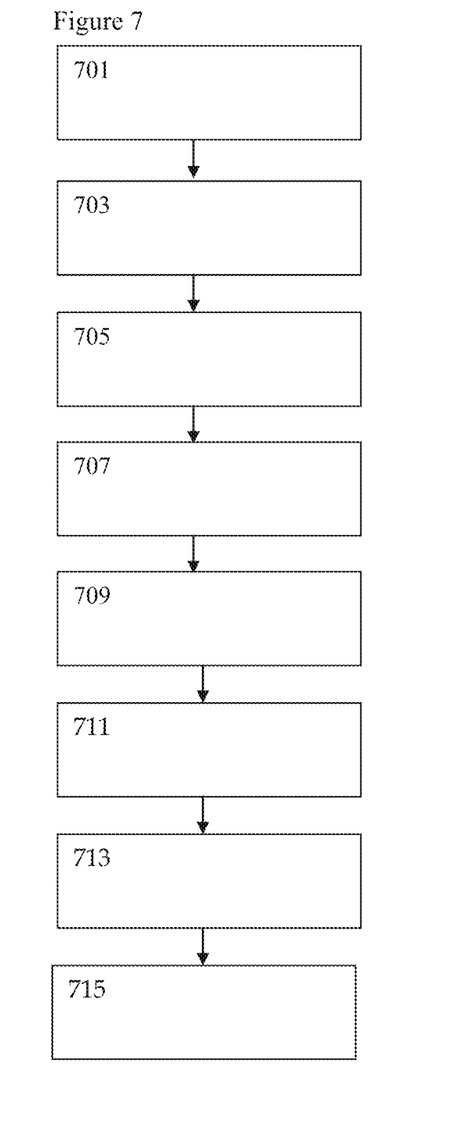
FIG. 7 is a flowchart illustrating a preferred embodiment of the claimed invention.

FIG. 7 illustrates the process of utilizing the claimed invention to report cardiac risk factors as indicated by Troponin and TMAO in conjunction with managing the administration of a pharmaceutical illustrated by metformin. Sample preparation step (701) begins with the user placing saliva on a sample collection means and the system stores the time of saliva sample capture. In the illustrative embodiment the saliva sample is captured by the user on a lateral flow sample strip enhanced with an optional glucose level indicator as well as Troponin aptamer. Pharmaceutical data capture step (703) is achieved by a patient entering the administration time and dosage information of the pharmaceutical presently administered to the patient. In the illustrative example a smartphone is used which may alternately be a personal computer or dedicated device. The pharmaceutical data capture may be inputted manually by the patient and may alternately be captured automatically by using near field communication (NFC) or alternate means.

The sample is sent by mail or otherwise transported to a central analysis facility and analyzed by liquid chromatography and mass spectrometry (LC/MS) during sample chemical analysis step (705) to determine body levels of metformin pharmaceutical and TMAO. While the illustrative example utilizes a centralized LC/MS analysis platform other foreseen and intended variants may utilize localized dedicated analysis platforms.

The remainder of Example 2 illustrated by FIG. 6 takes place in a computational or cloud computing environment. During data analysis step (707) body levels of Troponin, TMAO and of the pharmaceutical metformin are analyzed against time of pharmaceutical administration and amount of administration together with body glucose levels. Data transmission step (709) transmits the user body Troponin, TMAO and metformin level results to the user's preferred computational device including smartphone and smart watch. Data reporting step (711) provides the user with body Troponin, TMAO and metformin levels as a function of time. Optional data alert/feedback gathering step (713) reports abnormal or medically dangerous cardiac risk levels to the user as well as medical providers and designated family members and provides an opportunity for gathering user feedback. Data mining step (715) provides a deeper analysis into cardiac risk factors indicated by Troponin and TMAO levels in conjunction with pharmaceutical administration as a function of time and behavior as greater data is collected by the system.

In a more specific illustrative embodiment, sample preparation step (701) begins with a user placing a saliva sample collection means in the mouth to collect saliva and takes a digital photo of the lateral flow sample strip with a smartphone. The strip contains glucose sensing means as well as Troponin aptamers according to the claimed invention. After exposure to saliva the user takes a photo of the strip which captures the time of strip exposure and provides time and body glucose and Troponin data to the system in real time. The saliva capture means can be associated to the system by way of 2D bar code, machine readable numbers or other identifiable characteristics. Pharmaceutical data capture step (703) takes place with the user inputting pharmaceutical details of pharmaceutical dosage and latest time of administration. Input may be through smartphone, smart watch, stand alone computer or other dedicated computing device. After saliva exposure and smartphone photo capture the sample is placed into a prepaid envelope provided during purchase in the consumer packaging and is sent by mail or otherwise transported to a central analysis facility and analyzed by liquid chromatography and mass spectrometry (LC/MS) during sample chemical analysis step (705). Unlike blood or other biological material collection, the sample is safe at room temperature and does not create hazardous waste handling concerns.

FIG. 5 illustrates the potential for mismatch between pharmaceutical administration and optimal drug levels for glucose management. FIG. 6 is representative of the healthier and more beneficial alignment of metformin drug levels. A primary objective of the system of FIG. 7 is to translate the saliva capture cardiac risk factors identified by Troponin and TMAO in conjunction with pharmaceutical data into actionable lifestyle changes to target drug levels for optimal effect. Once the drug levels are determined, data analysis step (707) takes place in a cloud computing environment to analyze body levels of pharmaceutical against time of administration and body glucose levels to determine the best time when the drug should be taken for optimal beneficial effect. The results are wirelessly transmitted over the internet during data transmission step (709) and the user's smartphone or smartwatch user interface displays a high level metadata analysis during data reporting step (711). Unlike traditional Physician's Desk Reference (PDR) or pharmaceutical packet insert materials, the data is presented in plain language and can be as simple as "You've been taking your pill at 4:00 PM. Why don't you try it at 8:00 AM and see if you feel better?"

Use of the claimed system is an iterative process, the more times the user provides results the more powerful the data becomes for user lifestyle wellness management. Optional data alert/feedback gathering step (713) is available to alert the user, designated family members and medical providers if critical overdose or dose omission is detected during sample analysis. Feedback can also be obtained as a result of change in behavior and can be as simple as the system asking the user "Now that you are taking your pill at 8:00 AM, do you feel better?" Data mining step (715) provides a deeper analysis into pharmaceutical administration as a function of time and behavior as greater data is collected by the system. While artificial intelligence cloud computing provides a computationally powerful tool, the smartphone/smart watch user interface report of data aggregation is intended to be simple by design. Aggregate results in this illustrative example are provided regularly in a simple format as further illustrated by FIG. 11 and FIG. 12.

Figure 8:
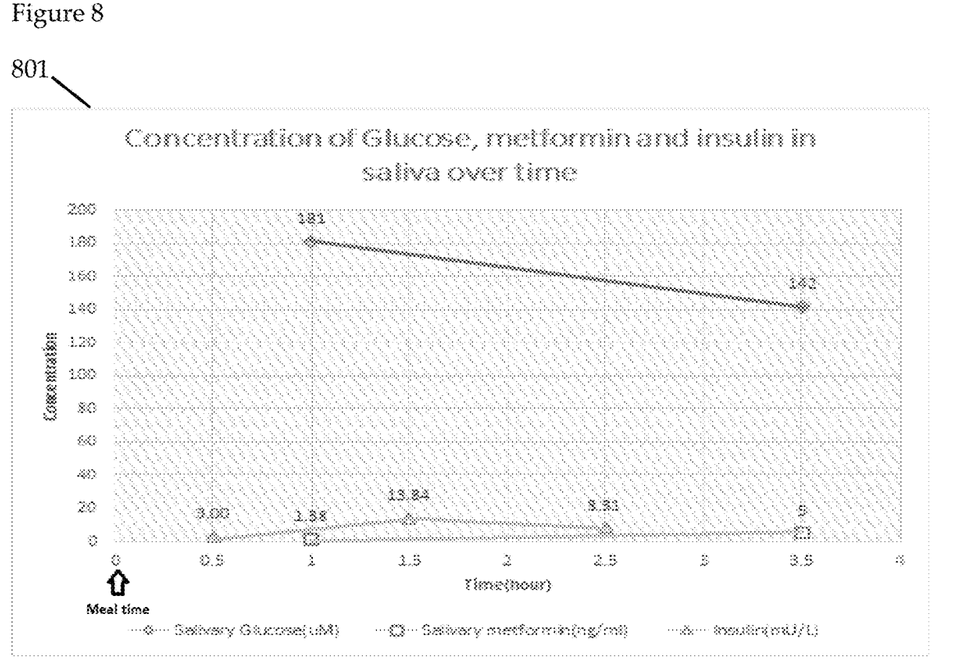
FIG. 8 is a graphical chart illustration of saliva derived metformin, glucose and insulin levels plotted by time.

FIG. 8 reflects an alternate embodiment of the claimed invention where locally obtained glucose results are augmented with subsequent pharmaceutical and insulin results determined by LC/MS and ELISA.

Example 3

In a third illustrative example, expanded personalized wellness information is obtained via combination test for diabetes related biomarkers including insulin, glucose, Metformin, TMAO and troponin. A saliva based lateral flow test strip upper detection layer captures glucose levels via an enzymatic test in conjunction with troponin levels by aptamer. Both glucose and troponin are captured by the user in real time. A lateral flow test strip lower level is analyzed remotely using traditional analytical chemistry techniques wherein LC/MS is used for TMAO, insulin and pharmaceutical detection and can be supplemented with DNA and RNA sequencing of the saliva sample as well as optional ELISA analysis. In the third illustrative example the presence or absence of a cardiac drug is determined.

Figure 9:
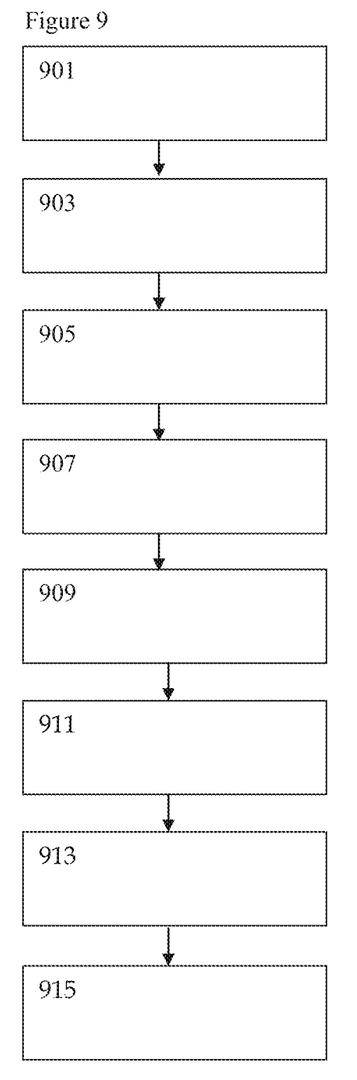
FIG. 9 is a flowchart illustrating a preferred embodiment of the claimed invention.

In FIG. 9, sample preparation step (901) begins with a user in need of medical monitoring placing a saliva sample collection means in the mouth to collect saliva and takes a digital photo of the sample strip with a smartphone. The strip contains one or more troponin aptamers embedded in the saliva collection device in combination with enzymatic glucose detection capabilities, both of which can undergo an optical or machine readable detection upon hybridization. After exposure to saliva the user takes a photo of the lateral flow sample strip which captures the time of strip exposure and provides capture time and optional aptamer data to the system. The lateral flow saliva capture means can be associated to the system by way of 2D bar code, machine readable numbers or other identifiable characteristics. Pharmaceutical data capture step (903) takes place with the user inputting pharmaceutical details of dosage and latest time of administration. Input may be through smartphone, smart watch, stand alone computer or other dedicated computing device. After saliva exposure and smartphone photo capture the sample is placed into a prepaid envelope provided during purchase in the consumer packaging and is sent by mail or otherwise transported to a central analysis facility and analyzed by liquid chromatography and mass spectrometry (LC/MS) for insulin, pharmaceutical illustrated in this embodiment by Metformin and TMAO detection as well as optional genetic sequencing during sample chemical and genetic analysis step (905). Insulin levels may be further characterized by antibody testing as well as further complementary enzymatic analysis of glucose levels. Unlike blood or other biological material collection, the saliva sample is safe at room temperature and does not create hazardous waste handling concerns.

Data analysis step (907) takes place in a cloud computing environment to analyze body levels of one or more pharmaceutical against time of administration and aptamer and/or genetic sequence indicated and genetic sequencing indicated conditions to determine the best time when the drug should be taken for optimal beneficial effect. In a foreseeable and intended embodiment the presence or absence of pharmaceutical carriers as well as multi-drug detection is carried out by the LC/MS system to determine if the pharmaceutical product is counterfeit and if the user is at risk from multi-drug cross reactions. In an intended alternate embodiment the presence or absence of illicit substances is also detected. Furthermore, the genetic sequencing and data analysis of the saliva sample allows for detection of bacterial and viral infections by screening for miRNA and DNA targets of interest.

The results are wirelessly transmitted over the internet during data transmission step (909) and the user's smartphone or smartwatch user interface displays a high level metadata analysis during data reporting step (911).

Use of the claimed system is an iterative process, the more times the user provides results the more powerful the data becomes for user lifestyle wellness management. Optional data alert/feedback gathering step (913) is available to alert the user, designated family members and medical providers if critical troponin and/or TMAO levels are exceeded in conjunction with overdose, dose omission or counterfeit pharmaceutical product detectio during sample analysis by screening for both pharmaceutical product as well as commonly used pharmaceutical carriers. Data mining step (915) provides a deeper analysis into drug administration as a function of time and behavior as greater data is collected by the system. While artificial intelligence cloud computing provides a computationally powerful tool, the smartphone/smart watch user interface report of data aggregation is intended to be simple by design. Aggregate results in this illustrative example are provided in a simple format for improved user personalized health.

Figure 10:
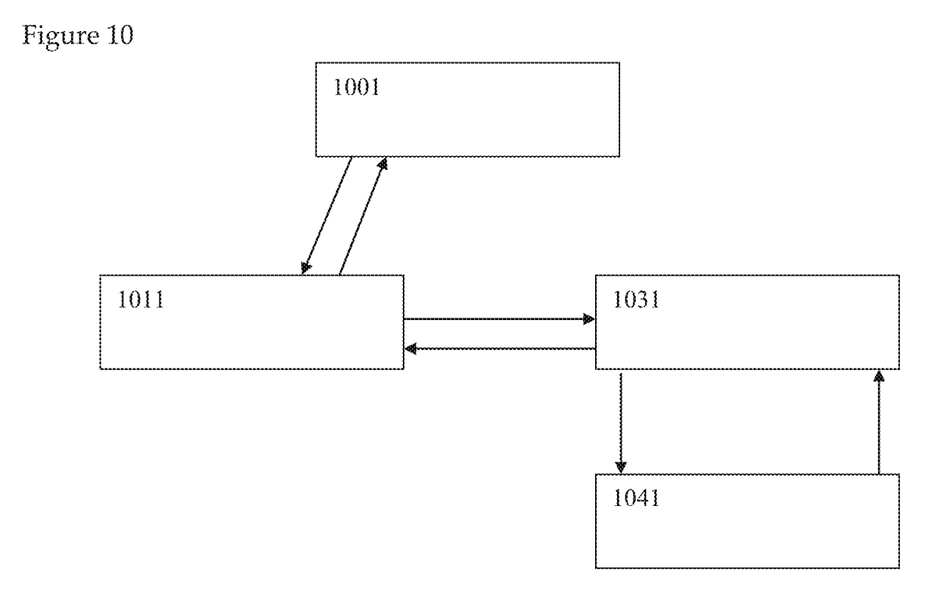
FIG. 10 is a flowchart illustrating a preferred embodiment of the claimed invention.

In FIG. 10, results from saliva sample collection device (1041) are captured by personal communication device (1031) incorporating one or more central processing units, one or more cameras and internet connection means. Health sample analysis hardware (1001) further analyzes saliva sample collection device (1041) with results communicated through health sample interpretation software, artificial intelligence element and cloud computing element (1011) for interpretation and communication of saliva sample health care results (not shown). Saliva sample collection device (1041) may optionally contain one or more health sample detection chemicals as well as one or more health sample detection aptamers or DNA/RNA sample detection regions. Sample analysis hardware includes chromatography and mass spectrometry functionality and can additionally include genetic sequencing functionality.

Figure 11:
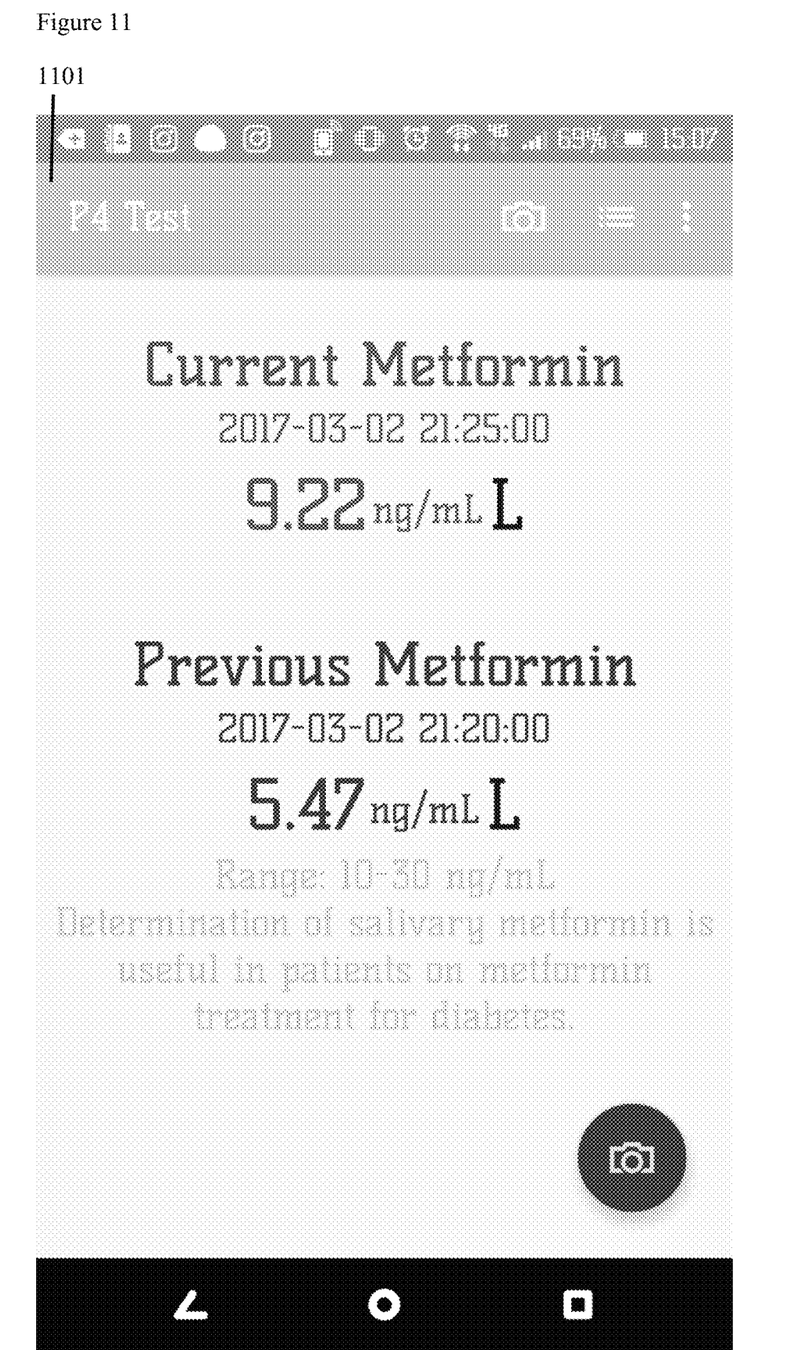
FIG. 11 is a diagram of a screen capture of a preferred embodiment of the claimed invention.

FIG. 11 is a diagram of a screen capture of a preferred embodiment of the claimed invention. In addition to providing real-time salivary glucose levels, P4 precision wellness information additionally incorporates pharmaceutical level results smartphone reported to the user's smartphone screen as illustrated. In the illustrative example current and previous metformin levels (1101) are represented.

Figure 12:
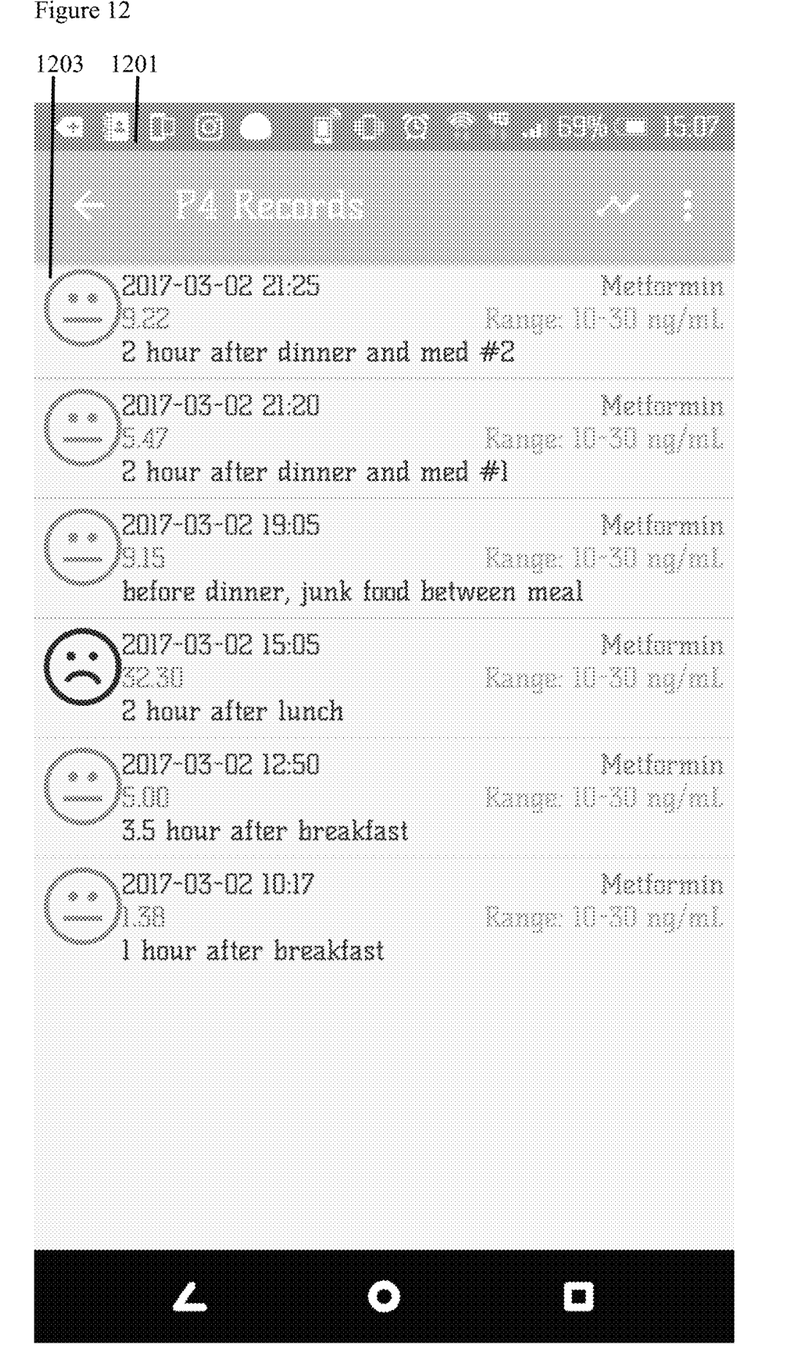
FIG. 12 is a diagram of a screen capture of a preferred embodiment of the claimed invention.

FIG. 12 is a diagram of a screen capture of a preferred embodiment of the claimed invention. Smartphone screen capture (1201) additionally incorporates a wide range of user pharmaceutical administration updates illustrated by easy to understand wellness icon (1203) summaries.

In the description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

INDUSTRIAL APPLICABILITY

The claimed invention has industrial applicability in the biomedical arts. In particular, the claimed invention is directly relevant to cardiac health and related therapeutic administration of pharmaceuticals for mitigation of and therapeutic effects against cardiac diseases.

---

Sequence Listing

Length: 25
Type: DNA
Organism: Artificial Sequence
Description of Artificial Sequence: Synthetic oligonucleotide

SEQ ID NO: 1
5'-GGG ATG GGG TGG GTG GCC AGC GAT T-3'

Length: 25
Type: DNA
Organism: Artificial Sequence
Description of Artificial Sequence: Synthetic oligonucleotide

SEQ ID NO: 2
5'-TTA GGG GTG GTG TGG TTG GCA ATT C-3'

I claim:

1. A method for personal health data monitoring comprising the steps of:

exposing a saliva sample to a lateral flow sample strip, capturing a Troponin marker by flowing the saliva sample on the lateral flow sampling strip comprising a Troponin aptamer configured to bind to a target skeletal Troponin I protein, wherein the binding is indicated by capture lines in the presence of the target skeletal Troponin I protein, mailing the lateral flow sample strip to a remote location for further analysis, analyzing said lateral flow sample strip for body levels of TMAO (trimethylamine-N-oxide), transmitting user body TMAO level results to a user's smartphone device, wherein said smartphone device incorporates one or more central processing units having an internet connection operatively connected to health sample subsequent analysis hardware and health sample interpretation software configured for TMAO and Troponin analysis wherein the user's TMAO levels are presented as a function of time.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide construct created by
      rational design

<400> SEQUENCE: 1
gggatggggt gggtggccag cgatt                                              25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide construct created by
      rational design

<400> SEQUENCE: 2
ttaggggtgg tgtggttggc aattc                                              25
```